United States Patent [19]

Nakagawa et al.

[11] 4,133,736
[45] Jan. 9, 1979

[54] APPARATUS FOR DETERMINING AN OXYGEN CONTENT

[75] Inventors: Masaru Nakagawa, Tama; Yasuaki Saito, Gamagori; Hideaki Okada, Habikino, all of Japan

[73] Assignees: Iijima Products M.F.G. Co., Ltd.; Okada Shigyo Co., Ltd., both of Japan

[21] Appl. No.: 853,909

[22] Filed: Nov. 22, 1977

[51] Int. Cl.$^2$ .................. G01N 1/24; G01N 27/30; G01N 27/46
[52] U.S. Cl. .................. 204/195 P; 73/421.5 R; 204/1 T; 204/195 R
[58] Field of Search .................. 204/1 P, 1 E, 195; 73/421.5 R

[56] References Cited

U.S. PATENT DOCUMENTS

| | | | |
|---|---|---|---|
| 2,457,707 | 12/1948 | Neuman et al. | 73/52 X |
| 2,786,355 | 3/1957 | Day et al. | 73/421.5 R |
| 3,071,530 | 1/1963 | Neville | 204/195 P |
| 3,203,248 | 8/1965 | Stutler et al. | 73/421.5 R |
| 3,374,678 | 3/1968 | McGuckin | 73/421.5 R |

FOREIGN PATENT DOCUMENTS 217028  7/1968  U.S.S.R. .................. 73/421.5 R

*Primary Examiner*—G. L. Kaplan

[57] ABSTRACT

An apparatus for determining oxygen content in a sealed container is disclosed. The apparatus comprises a sampling tube having a sampling zone which is provided with a pumping means, a change-over valve means for communicating the sampling zone selectively with either inlet or outlet path and a measuring instrument containing an electrode for oxygen determination and air-tightly connected to said sampling tube where one end of the outlet path is opened against the electrode.

6 Claims, 13 Drawing Figures

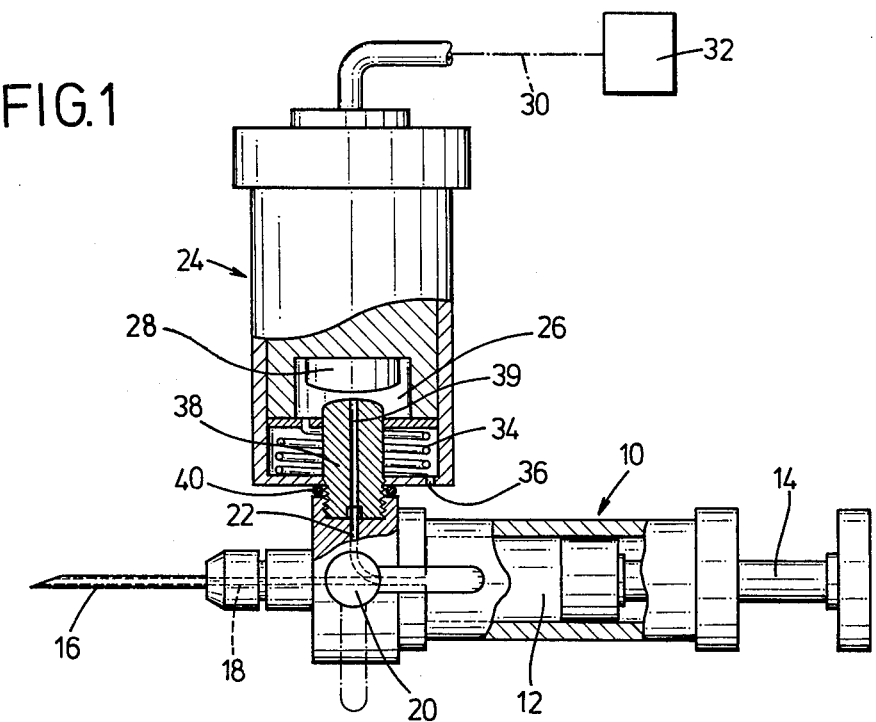

4,133,736

APPARATUS FOR DETERMINING AN OXYGEN CONTENT

BACKGROUND OF THE INVENTION

This invention relates to an apparatus for determining an oxygen content and, more particularly, to an apparatus suitable for use in analyzing the oxygen contained as an impurity in a sealed container in which food or the like is packed.

Recently, food or the like having improved shelf-life are commercially produced, using gas-displacement packing technique, and are conveniently supplied for general consumers. A range of 0.015 to 5% of oxygen content may be acceptable as impurity in the sealed container in which commodities are packed by gas-displacement packing. In determining the oxygen content, predetermined amount of samples are generally taken from the random products by means of a syringe and the like and analyzed by a gas chromatography where the samples inevitably come into contact with ambient atmosphere after sampling and before introduction into measuring part of the chromatographic apparatus, resulting in erroneous determinations. Further, chromatographic method is very complicated to operate. Therefore, an apparatus which permits easy operation and precise determinations has still now been expected.

In this specification, the term "the apparatus" means the apparatus for determining oxygen content, "the borer" means the borer for boring a hole to take a gas sample from the sealed container, "the grasping lever" means the lever for grasping the container by hand, and "the water pool unit" means the unit comprising water pool for preventing atmospheric air from contacting with the products to be analyzed.

Now, it has been found that an oxygen content in a sealed container, in which commodities are packed by gas-displacement packing technique, can be easily and precisely determined by connecting a sampling tube such as a syringe with a measuring device in airtight manner, providing the sampling tube with a sampling zone in which a sample is introduced by a pumping means, connecting the sampling zone with either inlet or outlet path selectively through a change-over valve, providing the measuring device with a measuring zone therein, arranging an electrode for oxygen analysis in the measuring zone while connecting the measuring zone with the outlet path of the sampling tube in order to inject the sample to the electrode of the measuring zone via the outlet path by pumping the sample with the pumping means and by turning the change-over valve.

SUMMARY OF THE INVENTION

It is, therefore, a principal object of the present invention to provide an apparatus for determining oxygen content in a sealed container, which comprises a sampling tube having a sampling zone which is provided with a pumping means, a change-over valve means for communicating the sampling zone selectively with either inlet or outlet path and a measuring instrument containing an electrode for oxygen determination and air-tightly connected to said sampling tube where one end of the outlet path is opened against the electrode.

In the apparatus according to the invention, the inlet path preferably has a sucking needle. More preferably, the sucking needle is connected, as fully described hereinafter, to a borer for gas sampling or to a water pool unit for gas sampling, so as to take gas out of the air-tightly packed container such as a can, a bottle, an ampoule and the like while surely avoiding contact of sample gas with atmosphere.

Accordingly, another object of the invention is to provide an apparatus for determining oxygen content in combination with a borer for sampling of gas from an air-tightly packed container.

This another object is achieved by air-tightly connecting the borer to the inlet path for sample. The borer comprises a grasping lever which is provided along its longitudinal length with a fixed claw member, a tapped hole and a slot for receiving a slidable and movable claw member and a boring member adapted to fit into the tapped hole and provided along the center axis thereof with a threaded hole at its top portion and a tubular projection forming a boring rivet at its lower end. The tubular projection communicates with the threaded hole which receives at its bottom portion a filler of soft flexible material under depression by a plug fastened therein and has an aperture therethrough. The tubular projection is encompassed by a packing member of soft flexible material. In this case, the borer may be constructed in such a manner that the fixed claw member comprises a holding member pivotably connected to one end of the grasping lever and an engaging piece faced through an adjustable clearance with said holding member by means of an adjusting fastner.

Further object of the invention is to provide the apparatus for determining oxygen content in combination with a water pool unit for taking a sample gas with no contact with an ambient air.

This object is achieved by air-tightly connecting the gas sampling means to the inlet path for samples. The gas sampling means comprises a water pool for receiving a packed container to be sampled, a hollow needle for gas sampling which is vertically fixed at the bottom of the water pool so that a tip of the needle is positioned under the water level, a flexible slender pipe led from a fixed base of the hollow needle to the outside of the water pool and an adapter for air-tightly connecting an open end of the flexible tube to the sucking needle. In this means, it is preferred that the water pool contains therein a stand for holding the packed container at a predetermined position which permits the tip of the needle to reach at an appropriate depth in the container. Further, it is more preferred that the water pool contains therein a stand having a hole for receiving the needle and an opening means arranged on a part of the stand to open the packed container.

Another objects and advantages of the invention will become apparent from the following disclosure taken in conjunction with the accompanying drawings.

BRIEF DESCRIPTION OF THE DRAWINGS

FIG. 1 is a front view partially in sectioned of an embodiment of apparatus for determining oxygen content according to the invention;

FIG. 2a and 2b are sectional views of the borer for sampling of gas according to the invention;

FIG. 3a and 3b are bottom views of the borer for sampling of gas of FIGS. 2a and 2b;

FIGS. 4a and 4b are plan views of the borer of FIGS. 2a and 2b;

DESCRIPTION OF THE PREFERRED EMBODIMENT

Figure 2B:
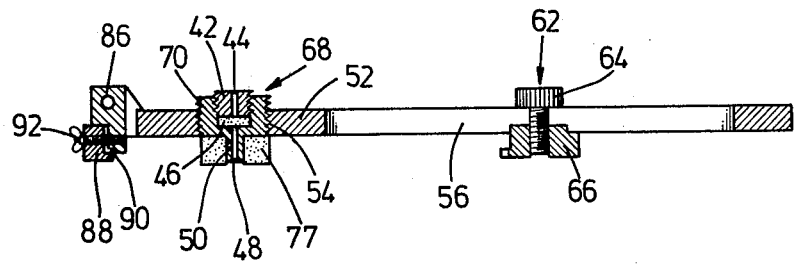

As shown in FIG. 1, a sampling tube 10, such as a syringe, has therein a sampling zone 12 which is provided with a pumping unit 14 and a part of the sampling zone 12 of the syringe 10 is provided with an inlet path 18 which is communicated with a sucking needle 16. At the middle portion of the inlet path 18, there is arranged a change-over valve 20 through which an outlet path 22 is led so that the inlet path 18 and the outlet path 22 are selectively connected with the sampling zone 12.

As hereinbefore described, the syringe 10 is airtightly communicated with the measuring device 24 in which a sealed measuring zone 26 is defined to face with a detecting end of an electrode 28 for oxygen analysis enclosed in the measuring device 24. The electrode 28 used in the invention is commercially available and composed of a lead-anode and a gold-cathode which are isolated from a sample by means of the Teflon film in which a potassium chloride solution is sustained as an electrolyte. The opposite end of the electrode 28 is connected with lead 30 to an amplifier 32 which is connected to a convenient indicating means for visual reading of measurement.

In the low portion of the measuring zone 26, a spiral delivery tube 34, for example in diameter of 0.5mm and in length between 50-100 cm, is arranged through a partition wall and the opposite ends of the tube 34 are communicated with the measuring zone 26 and a delivery port 36.

Furthermore, to the measuring zone 26 is attached a connecting tube 38 which is air-tightly connected to a lateral portion of the syringe 10 through a sealing O-ring 40. In this case, one end of the channel 39 of the connecting tube 38 communicates with the outlet path 22 of the syringe 10 and the opposite end thereof is opened against the electrode 28 received in the measuring zone 26.

Figure 5B:
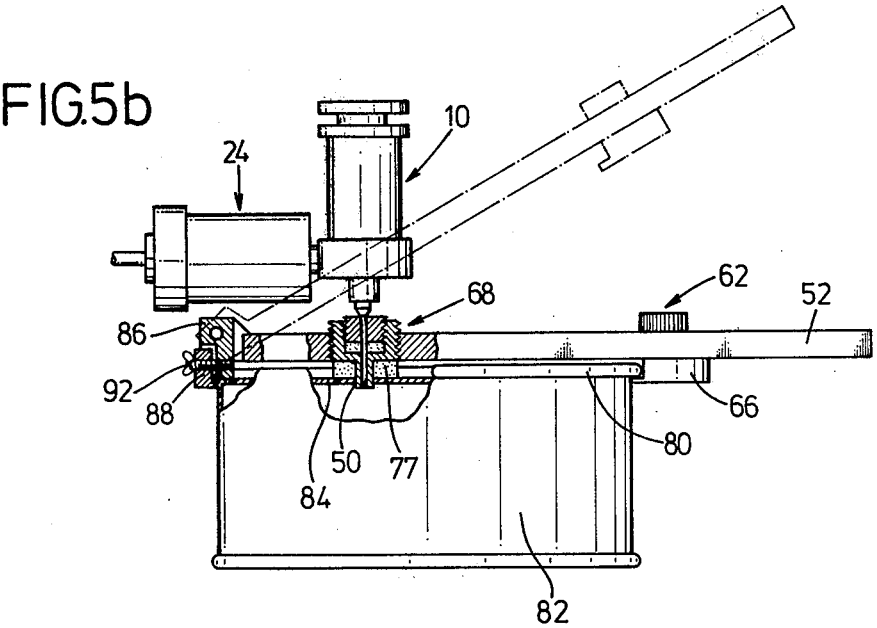
FIGS. 5a and 5b are lateral views in partially sectioned of the borer in engagement with the container.
Figure 5A:
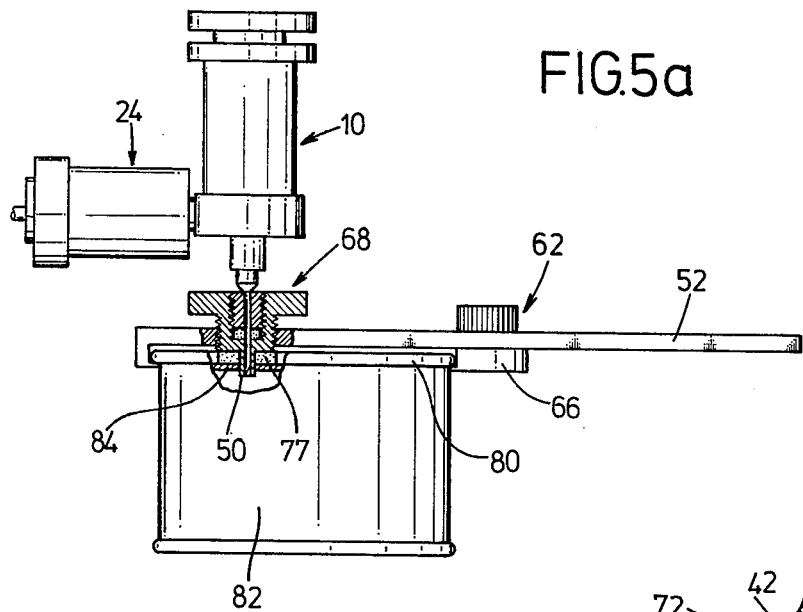

In order to positively pick up a sampling gas from the container with a perfect interception from an atmosphere the sucking needle may be inserted into a passage 44 of a plug 42 of the borer to pass through a filler 46 into a passage 48 of a projection 50 as best shown in FIGS. 2a and 5a.

A typical structure of the borer will be hereinafter described with reference to FIGS. 2a and 6.

In FIGS. 2a to 4a, the borer is comprised of a grasping lever 52 which at its longitudinal length is provided with a tapped hole 54 and a slot 56 with a given space therebetween. The grasping lever 52 at its one end has an end claw 58 fixed thereto through fasteners 60.

While in the slot 56 is slidably arranged a movable claw 62 which is comprised of a bolt 64 and a claw piece 66 screwed with the bolt 64. Thus, the fixed claw 58 and the movable claw 62 may rigidly embrace the rim portion of the container having different diameters.

The borer is further comprised of a boring member 68 which includes a bolt-like body 70 screwed into the tapped hole 54 of the grasping lever 52. The bolt body 70 is provided along its axis a threaded hole 72 in which bottom is placed the filler 46 of flexible material such as rubber, through which the passage 44 passes as hereinbefore described. Into the threaded hole 72 is screwed plug 42 to depress the filler 46 and the top end thereof, is provided with a screw slot 74. From the bottom of the bolt body 70 is extended a tubular projection 50 communicating with the passage 44 and encompassed by a packing member 77 of flexible material e.g. rubber, which is thicker than the height of the projection 50 and provided with a fitting center hole 78.

In an actual use of the borer, the fixed claw 58 of the grasping lever 52 is engaged with a rim 80 of the container 82 and the movable claw 62 is slided along the slot 56 to a predetermined position so that the rim 80 of the container 82 is rigidly embraced between the fixed claw 58 and the movable claw 62. Upon threading the boring member 68 the packing member 77 is at first made into contact with an upper lid 84 of the container 82 under gradual compression of the packing member 77 until the tubular projection 50 comes in contact with the upper lid 84. When the bolt body 70 is further threaded, the tubular projection 50 opens a hole through the upper lid 84 of the container 82, so that the packing member 77 is compressed between the container lid 84 and the bolt body 70 to hermetically seal the clearance therebetween for prevention of undesired air inflow into the container as well as escape of the gas therefrom. Further, the filler 46 prevents the ambient air from flowing into or the gas escaping out of the container through the center hole 78.

FIGS. 2b to 4b show another embodiment of the borer, where to one end of the grasping lever 52 is pivotably secured a holder 86 which is engaged with a claw member 88 with a clearance 90 adjustable by means of an adjusting rod screw 92.

When this modified borer is used, the grasping lever 52 at its one end is raised upwardly and the adjusting screw rod 92 is reluxed to enlarge the clearance 90 which is in turn positioned over the rim 80 of the container 82 so that the rim 80 is firmly embraced by the holder 86 and the claw member 88 under fastening of the rod screw 92 as shown in FIG. 5b. Then, the raised part of the grasping lever 52 is manually depressed making the packing member 77 into contact with the upper lid 84 of the container 82 until the tubular projection 50 comes into contact with the container lid 84 under compression of the packing member 77 and bores a hole in the upper lid 84. When the lever 52 is moved downwardly to reach a position parallel to the upper lid 84, the bolt 64 of the movable claw 62 is reluxed to slide the claw 62 along the slot 56 until the claw piece 66 is engaged with the periphery of the container. Then the bolt 64 is fastened to firmly grasp the container 82.

Figure 6:
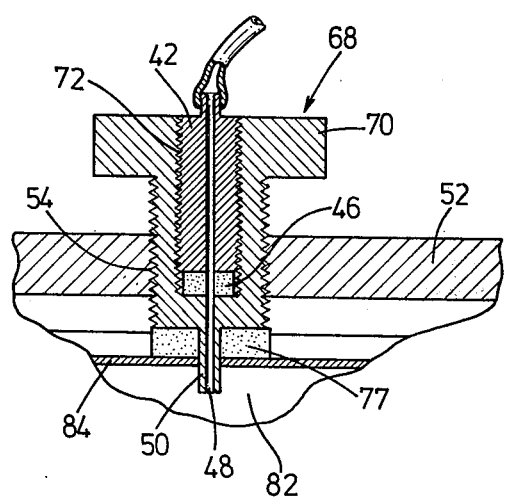
FIG. 6 is a fragmentarily enlarged sectional view of the borer of another embodiment.

When the gas pressure in the packed container is greater than the atmosphere pressure, it will be appreciated that the gas emitted from the container 82 is automatically introduced through the passages 48 and 44 into the inlet path of the apparatus without any aid of the pumping means as shown in FIG. 6.

Figure 3B:
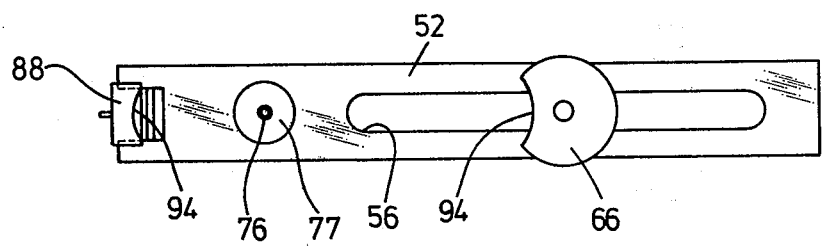
Figure 4B:
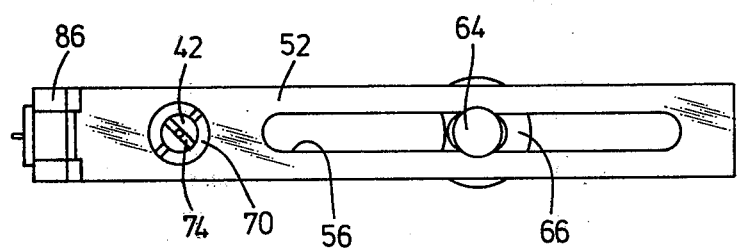

In order to grasp more firmly containers of various sizes, it is preferred to provide a cavity 94 in the engaging parts of the fixed and movable claw members 58 and 62 as best shown in FIGS. 3a and 3b. Further, to increase the durability of the borer, the fixed claw member, the tubular projection and the movable claw member may preferably be made of a hard steel which has been subject to a carburizing and hardening treatment to increase hardness. The fixed claw may be formed by bending the end of the grasping lever 52. Further, the packing member 77 may be preferably formed of fluorinated or silicone rubber to increase durability thereof.

Typical embodiments of the apparatus with the water pool unit are illustrated with reference to FIGS. 7 to 9.

Figure 7:
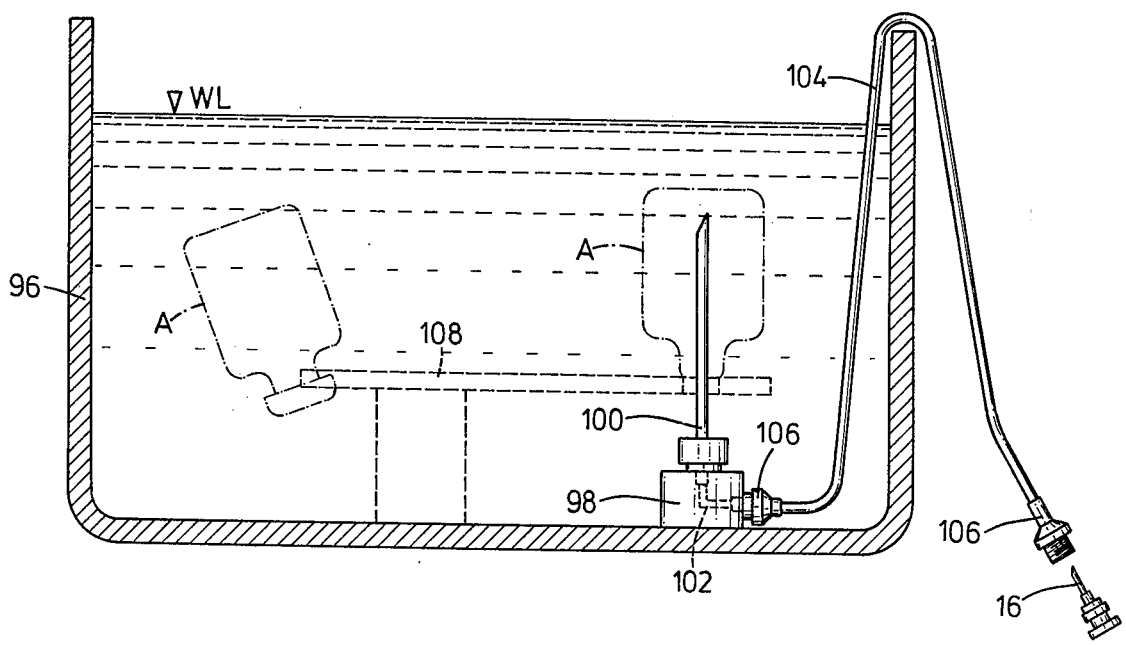
FIG. 7 is a sectional view of a water pool unit for taking sample gas in accordance with the invention.

FIG. 7 shows a basic arrangement of the water pool unit in which a water pool 96 contains a base member 98 on which a hollow needle 100 of predetermined length is vertically and removably stored. In the base member 98 is provided a passage 102 which communicates at the one end with the hollow needle 100 and at its opposite end with a flexible delivery tube 104 through an adaptor 106. The flexible delivery tube 104 is extended outside the water pool 96 through the water surface in the tank 96. The water level in the water pool 96 is always kept above the tip of needle 100. The water pool 96 may be preferably made of transparent material for visible purpose. A free end of the flexible delivery tube 104 is preferably mounted with a convenient adaptor 106, which is suitable for receiving the sucking needle 16 of the inlet path in the apparatus.

In operation of the water pool unit, a packed container A is immersed into the water pool 96 and the sealing cap is removed within the water, then the opened container is moved toward the needle 100 with the inlet positioned under the water level until the tip of the needle is inserted into the container through the opened inlet and arrives at the gaseous zone in the container so that a desired quantity of gas is taken by a sampling apparatus (not shown) arranged outside the water pool 96. In this operation, it is essential to evacuate the needle 100 and the flexible delivery tube 104 and then to fill with a purging fluid such as nitrogen gas and the like. Thus, a sample taken into the unit is immediately made into contact with the oxygen measuring electrode for the intended analysis of oxygen content.

In this embodiment, a stand 108 may be conveniently placed in the water pool 96 to secure the constant relative position between the needle 100 and the container A.

Figure 8:
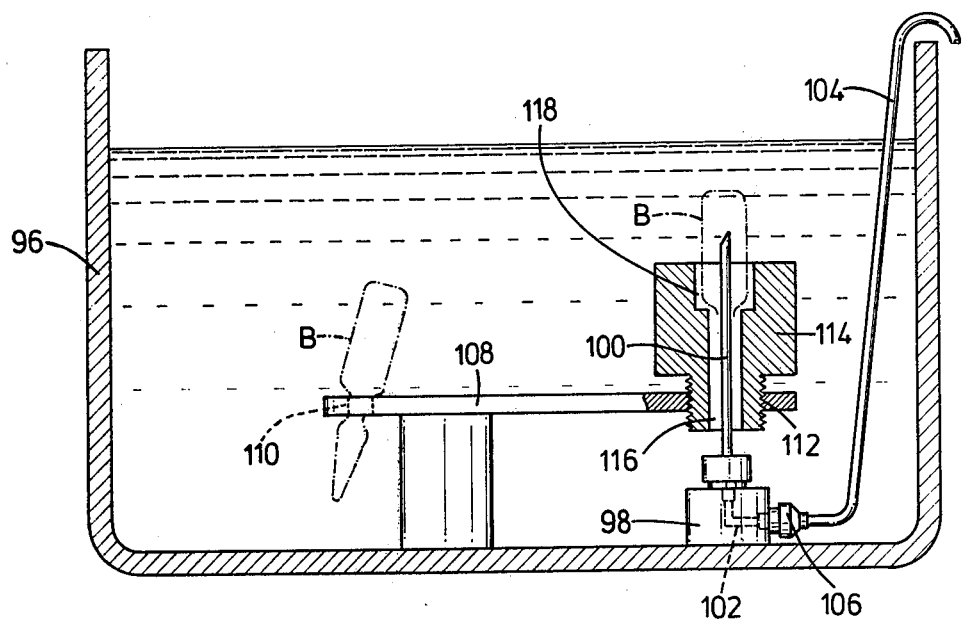
FIG. 8 is a sectional view of the water pool unit of another embodiment.
Figure 9:
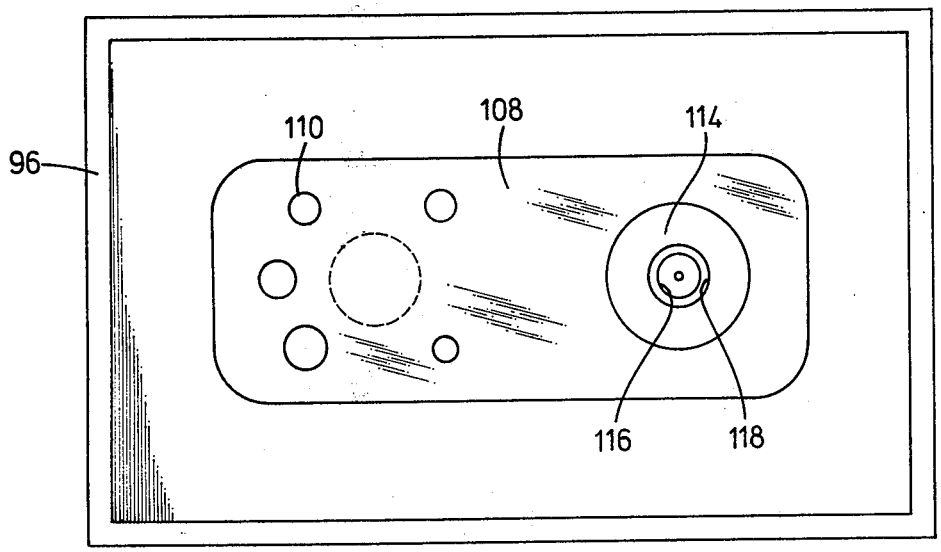
FIG. 9 is a plan view of the water pool unit of FIG. 8.

FIGS. 8 and 9 show another embodiment of the water pool unit which is exclusively used for ampoules. The basic arrangement of the embodiment is substantially the same as that shown in FIG. 7, where a plurality of holes 110 are opened at one end of the stand 108 in order to suspend ampoules for subsequent cutting operation. On the other hand, the stand 108 at its opposite end is provided with a threaded opening 112 into which an ampoule holder 114 is fastened. The ampoule holder 114 is made of transparent material and has a center hole 116 for receiving the needle 100 with an engaged portion 118 for receiving the ampoule B in a reversed position.

In accordance with this ampoule-retaining embodiment, the ampoule is similarly opened in water and moved toward the needle 100 which is subsequently inserted into the ampoule B until the tip of the needle 100 reaches the gaseous zone in the ampoule to take a required quantity of gas into a sampling apparatus (not shown) arranged outside the water pool unit.

In operation of the apparatus according to the invention to determine an oxygen content of a sealed container or a can, a bottle or an ampoule in which food or the like is packed, the changeover valve 20 is turned (to the position A as shown in FIG. 1) to communicate the sampling zone 12 with the inlet path 18 and the sucking needle 16 which is in turn inserted into the sealed container (not shown) or the sucking needle 16 is connected to the passage 44 of the borer or the adapter 106 of the water pool unit as described above hereinbefore so that a required quantity of sample is introduced into the sampling zone 12 by means of the pumping unit 14 through the path which has been previously purged with an inert gas such as nitrogen.

Thereafter, the change-over valve 20 is turned (to the position B as shown in FIG. 1) to communicate the sampling zone 12 with the outlet path 22 and the pumping unit 14 is depressed to eject the sample gas in the sampling zone 12 for the measuring electrode 28 through the outlet path 22. In the electrode 28 of the measuring zone 26, oxygen of the ejected sample penetrates into the thin membrane of the electrode and diffuses into the cathode for gradual consumption therein with the redox reaction. When the consumption rate of oxygen in the electrode is greater than the diffusion rate of oxygen in the sample, the oxygen concentration in the vicinity of the electrode becomes lower than that of the sample remote from the electrode, resulting in an incomplete reaction for which reason, the pumping operation of the pump unit 14 should be kept constant. The current generated due to the consumption of oxygen is supplied through the lead 30 to an amplifier 32 for the appropriate amplification thereby to indicate the oxygen concentration visually or in any other means.

The sample injected into the measuring zone 26 is emited from the delivery port 36 through the spiral tube 34 having less diameter with sufficient length which does not permit any entrance of ambient air from the port 36 into the measuring zone and thus no check valve is required. Further, the spiral tube 34 serves to uniform the delivery rate of the sample from the measuring zone 26 into the atmosphere.

According to the apparatus for determining oxygen content of the invention, the let-in and let-out operation of the sample is carried out by merely turning the change-over valve and the desired analysis may be performed without making the sample into contact with the ambient air.

Furthermore, according to the apparatus of the invention in combination with the borer or the water pool unit the containers such as can, bottle, ampoule and the like may be held firmly with sufficient packing and water pool function which effectively prevent the sample from contacting with the ambient air.

While certain preferred embodiments of the invention have been illustrated by way of example in the drawings and particularly described, it will be understood that modifications may be made in the constructions and that the invention is no way limited to the embodiments shown.

What we claim is:

1. An apparatus for determining the oxygen content in a sealed container, being an integral unit comprising a sampling tube having a sampling zone provided with pumping means, a single multipositionable change-over valve for communicating the sampling zone selectively with either an inlet or an outlet path, an oxygen measuring device containing an electrode for oxygen determination air-tightly but removably connected to said sampling tube, one end of said outlet path being opened against the electrode, said inlet path having a sucking needle located at its sample receiving end.

2. An apparatus as claimed in claim 1, wherein the inlet path includes a borer connected air-tightly to said sucking needle for boring a container to extract a gas sample, said borer comprising a grasping lever which is provided along its longitudinal length with a fixed claw member, a tapped hole and a slot for receiving a slidable and movable claw member and a boring member adapted to fit into the tapped hole and provided along the center axis thereof with a threaded hole at its top portion and a tubular projection forming a boring rivet at its lower end, said tubular projection communicating with the threaded hole which receives at its bottom portion a filler of soft flexible material under depression by a plug fastened therein and having an aperture therethrough, said tubular projection being encompassed by a packing member of soft flexible material.

3. An apparatus as claimed in claim 2, wherein the fixed claw member comprises a holding member pivotably connected to one end of the grasping lever and an engaging piece faced through an adjustable clearance with said holding member by means of an adjusting fastner.

4. An apparatus as claimed in claim 1, wherein the inlet path comprises the sucking needle and the gas sampling means air-tightly connected thereto, said gas sampling means comprising a water pool for receiving a packed container to be sampled, a hollow needle for gas sampling which is vertically fixed at the bottom of the water pool so that a tip of the needle is positioned under the water level, a flexible slender pipe led from a fixed base of the hollow needle to the outside of the water pool and an adapter for air-tightly connecting an open end of the flexible tube to the sucking needle.

5. An apparatus as claimed in claim 4, wherein the water pool contains therein a stand for holding the packed container at a predetermined position which permits the tip of the needle to reach at an appropriate depth in the container.

6. An apparatus as claimed in claim 5, wherein said water pool contains therein a stand having a hole for receiving the needle and an opening means arranged on a part of the stand to open the packed container.

* * * * *